United States Patent
Li et al.

(10) Patent No.: US 11,592,428 B2
(45) Date of Patent: Feb. 28, 2023

(54) EVALUATION METHOD FOR IMPACT OF EMISSION CONTROL ON AIR QUALITY, DEVICE AND STORAGE MEDIUM THEREOF

(71) Applicant: SOUTHERN UNIVERSITY OF SCIENCE AND TECHNOLOGY, Guangdong (CN)

(72) Inventors: Ying Li, Shenzhen (CN); Yushan Song, Shenzhen (CN)

(73) Assignee: SOUTHERN UNIVERSITY OF SCIENCE AND TECHNOLOGY, Shenzhen (CN)

(*) Notice: Subject to any disclaimer, the term of this patent is extended or adjusted under 35 U.S.C. 154(b) by 345 days.

(21) Appl. No.: 16/897,063

(22) Filed: Jun. 9, 2020

(65) Prior Publication Data
US 2020/0393434 A1 Dec. 17, 2020

(30) Foreign Application Priority Data
Jun. 13, 2019 (CN) .......................... 201910509246.4

(51) Int. Cl.
*G01N 33/00* (2006.01)
*G01N 1/22* (2006.01)
(Continued)

(52) U.S. Cl.
CPC ....... *G01N 33/0075* (2013.01); *G01N 1/2273* (2013.01); *G01W 1/02* (2013.01); *G06F 17/18* (2013.01)

(58) Field of Classification Search
CPC ............ G01N 33/0075; G01N 1/2273; G01N 33/0004; G01N 33/0073; G01N 30/8662;
(Continued)

(56) References Cited

U.S. PATENT DOCUMENTS

2017/0263116 A1* 9/2017 Lorenz ............. G08G 1/096883
2018/0321347 A1* 11/2018 Wang .................. G01R 33/5608

FOREIGN PATENT DOCUMENTS

CN 106845371 A * 6/2017 ............. G01D 21/02
CN 107563562 A * 1/2018
(Continued)

OTHER PUBLICATIONS

First Office Action dated Jun. 1, 2022, in corresponding to Chinese Application No. 201910509246.4, 11 pages (including English Translation).

*Primary Examiner* — Jeffrey P Aiello
(74) *Attorney, Agent, or Firm* — Maier & Maier, PLLC

(57) ABSTRACT

An atmospheric pollution emission control effect evaluation method, device and storage medium, including: carrying out meteorological condition frequency statistics of data collected from meteorological station, obtaining meteorological condition frequency distribution information; obtaining pollutant concentration information, performing pollutant concentration distribution statistics to obtain pollution concentration distribution information and pollution concentration variation information; decomposing effects of meteorological factors and non-meteorological factors according to meteorological condition frequency distribution information, pollution concentration distribution information and pollution concentration variation information, to obtain meteorological and non-meteorological contribution information; constructing source emission control effect evaluation data set according to meteorological condition frequency distribution information, pollution concentration distribution information, meteorological and non-meteorological contribution information. Accordingly, emission control effect can be quantitatively evaluated based on observation data. Emission increasing effect and contribu-
(Continued)

tion of meteorological changes to variation of average pollution level can be quantified.

10 Claims, 4 Drawing Sheets

(51) Int. Cl.
*G01W 1/02* (2006.01)
*G06Q 50/26* (2012.01)
*G06F 17/18* (2006.01)

(58) Field of Classification Search
CPC ............... G01N 1/26; G01N 2001/021; G01N 2001/2223; G01W 1/02; G01W 1/00; G06F 17/18; G06Q 50/26; G06Q 99/00; Y02W 90/00; Y02A 50/20; Y02T 10/40; Y02T 10/12
USPC ...... 73/1.06; 701/117; 702/2–3, 23–24, 109, 702/188–189; 703/2, 13
See application file for complete search history.

(56) References Cited

FOREIGN PATENT DOCUMENTS

| | | | | |
|---|---|---|---|---|
| CN | 107563562 A | | 1/2018 | |
| CN | 107942411 A | * | 4/2018 | ............. G01W 1/10 |
| CN | 107942411 A | | 4/2018 | |
| JP | 2005172442 A | * | 6/2005 | |
| JP | 2005172442 A | | 6/2005 | |

* cited by examiner

EVALUATION METHOD FOR IMPACT OF EMISSION CONTROL ON AIR QUALITY, DEVICE AND STORAGE MEDIUM THEREOF

CROSS-REFERENCES TO RELATED APPLICATIONS

This application claims the priority of Chinese patent application no. 201910509246.4, filed on Jun. 13, 2019, the entire contents of all of which are incorporated herein by reference.

FIELD

The present disclosure relates to the technical field of atmospheric environment, and more particularly, to an evaluation method for an impact of emission control on air quality, a device and a storage medium thereof.

BACKGROUND

Air pollution is a complex pollution phenomenon, when a plurality of pollutants in atmosphere reach a certain concentration, the air pollution will have an adverse impact on human life, production and health. In order to ensure an air quality and protect public health, governments at all levels have adopted a series of measurements to reduce a plurality of anthropogenic emissions of the pollutants. However, since a plurality of factors affecting a concentration of the pollutants are very complex, also an effect of a plurality of emission factors and an effect of a plurality of meteorological factors are often mixed together, it is of a great significance for a government's air quality management to evaluate an emission control effect to air quality changes.

In the prior art, the effects to the air quality changes by the emission factors have been evaluated by a plurality of emission-based numerical models and a plurality of observation-based statistical methods. However, the numerical models are subject to a plurality of model errors and uncertainties of a model input, while for an observation-based regression statistical method, it is hard to reconstruct a factor reasonably representing an emission variation.

Therefore, the prior art needs to be improved and developed.

SUMMARY

The technical problem to be solved in the present disclosure, aiming at the defects of the prior art, provides an evaluation method for the impact of emission control on air quality, a device and a storage medium thereof, in order to solve a problem in the prior art that it is difficult to quantify the effects to the air quality generated by the emission control factors, when separating the effects to the air quality changes generated by the emission factor and by the meteorological factor.

One aspect of the present disclosure provides an evaluation method for the impact of emission control on air quality. The method includes: performing a meteorological condition frequency statistics on data collected from a meteorological station, and obtaining meteorological condition frequency distribution information; acquiring pollutant concentration information, and performing a pollutant concentration distribution statistics based on the pollutant concentration information and the meteorological condition frequency distribution information, to obtain pollution concentration distribution information and pollution concentration variation information; performing a decomposition of an effect of a plurality of meteorological factors and an effect of a plurality of non-meteorological factors, according to the meteorological condition frequency distribution information, the pollution concentration distribution information and the pollution concentration variation information, to obtain meteorological and non-meteorological contribution information; constructing a source emission control effect evaluation data set, based on the meteorological condition frequency distribution information, the pollutant concentration distribution information, and the meteorological and non-meteorological contribution information.

Second aspect of the present disclosure provides an evaluation device for the impact of emission control on air quality, the evaluation device comprises: a processor and a memory connecting to the processor, the memory has an evaluation program for the impact of emission control on air quality stored, when the evaluation program for the impact of the emission control on the air quality is executed by the processor, a plurality of following steps will be achieved: performing a meteorological condition frequency statistics on the data collected from a meteorological station, obtaining meteorological condition frequency distribution information; acquiring pollutant concentration information, and performing a pollutant concentration distribution statistics based on the pollutant concentration information and the meteorological condition frequency distribution information, before obtaining pollution concentration distribution information and pollution concentration variation information; performing a decomposition of an effect of a plurality of meteorological factors and an effect of a plurality of non-meteorological factors, to obtain meteorological and non-meteorological contribution information, according to the meteorological condition frequency distribution information, the pollution concentration distribution information and the pollution concentration variation information; constructing a source emission control effect evaluation data set, based on the meteorological condition frequency distribution information, the pollutant concentration distribution information, the meteorological and non-meteorological contribution information; the processor is applied to calling a command of the evaluation program for the impact of emission control on air quality.

Third aspect of the present disclosure further provides a storage medium, wherein the storage medium has a computer program stored that may be executed to implement the evaluation method for the impact of emission control on air quality as described above.

DETAILED DESCRIPTION

In order to make the purpose, technical solution and the advantages of the present disclosure clearer and more explicit, further detailed descriptions of the present disclosure are stated here, referencing to the attached drawings and some embodiments of the disclosure. It should be understood that the detailed embodiments of the disclosure described here are used to explain the present disclosure only, instead of limiting the present disclosure.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Figure 1:
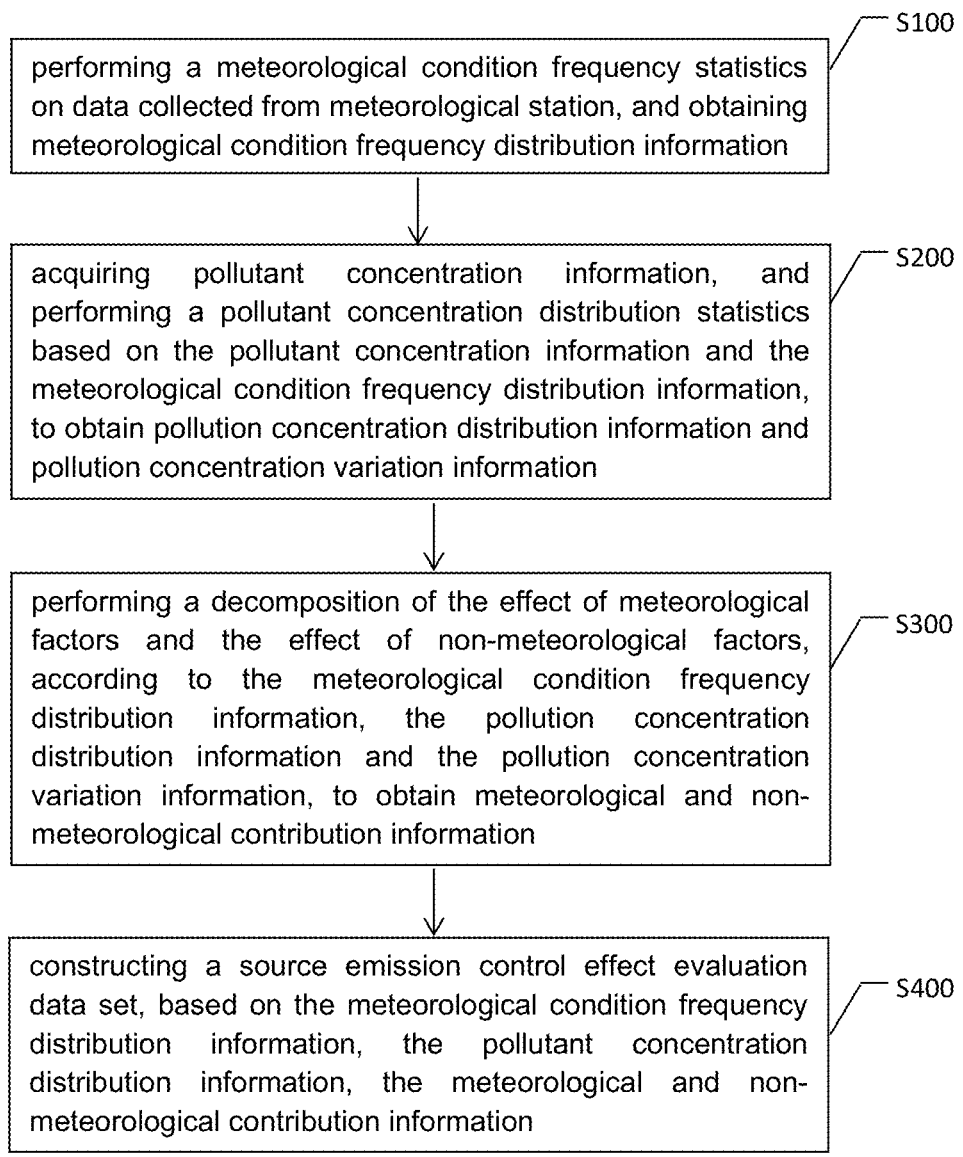
FIG. 1 illustrates a flow chart on an embodiment of the evaluation method for impact of emission control on air quality as provided in the present disclosure.

Referencing to FIG. 1, FIG. 1 illustrates a flow chart on an embodiment of an evaluation method for an impact of emission control on air quality as provided in the present disclosure. Shown as FIG. 1, the evaluation method for the impact of emission control on air quality, comprising:

S100, performing a meteorological condition frequency statistics on a plurality of data collected from a meteorological station, and obtaining meteorological condition frequency distribution information;

S200, acquiring pollutant concentration information, and performing a pollutant concentration distribution statistics based on the pollutant concentration information and the meteorological condition frequency distribution information, to obtain pollution concentration distribution information and pollution concentration variation information;

S300, performing a decomposition of the effect of a plurality of meteorological factors and the effect of a plurality of non-meteorological factors, according to the meteorological condition frequency distribution information, the pollution concentration distribution information and the pollution concentration variation information, to obtain meteorological and non-meteorological contribution information;

S400, constructing a source emission control effect evaluation data set, based on the meteorological condition frequency distribution information, the pollutant concentration distribution information, the meteorological and non-meteorological contribution information.

The present disclosure uses a plurality of data collected from an air quality monitoring station, combining with a plurality of data collected from a meteorological station, to decompose a contribution of the meteorological factors and a contribution of the non-meteorological factors, before finally forming a data set, which provides a technical support and a data support to rapidly assess the source emission control effect; being able to not only quantify the source emission control effect, but also quantify the effects of increased emissions and the contribution of meteorological changes to an variation of an average pollution level.

In an embodiment of the present disclosure, in the step S100, a plurality of data collected from a meteorological station is first obtained, before grouped according to a plurality of meteorological conditions, and a frequency of occurrence of the meteorological conditions in each group is then calculated. The data collected from the meteorological station comprises an hourly wind speed, a wind direction, a temperature, humidity, a precipitation data and more, from a single meteorological station. While a plurality of grouping criteria for the meteorological conditions include: whether there is precipitation happening, wind speed, wind direction, temperature and humidity. There are a plurality of methods to obtain the data collected from the meteorological station, including: obtaining from public data of a Global Telecommunication System (GTS), or directly obtaining meteorological data after signing an agreement with a Meteorological Bureau.

Specifically, when there is precipitation happening, it is separately listed as a group; when there is no precipitation happening, it is grouped according to the wind speed, the wind direction, the temperature, and the humidity. The wind speed is divided into low wind speed, medium wind speed and high wind speed, the wind direction is decided by dividing 0-360° into 12 parts, the temperature is divided into a low temperature and a high temperature, and the humidity is divided into low humidity and high humidity. Therefore, when there is no precipitation happening, a number of groups will be 3×12×2×2=144; together with a precipitation group, thus a total number of groups will be 145.

Then a formula will be applied to calculating the frequency of occurrence of the meteorological conditions in each group, a calculation formula is:

$$f(i) = \frac{N_i}{\sum N_i}$$

wherein, f(i) denotes a frequency of occurrence of the meteorological conditions in a group i, $N_i$ denotes an occurrence time of the meteorological conditions in the group i during a preset time period; the preset time period may be set by yourself, may be one year or one season or one quarter, or other time periods.

The frequencies of occurrence of the meteorological conditions f(i) in all groups are composed together into a meteorological condition frequency distribution vector F, and the meteorological condition frequency distribution vector F is saved as the meteorological condition frequency distribution information.

It is understandable that, during a specific implementation, the meteorological factors including "the wind speed, the wind direction, the temperature, the humidity, and the precipitation" may be increased or decreased, depending on a specific situation. In some embodiments, a plurality of other meteorological factors may be included, including a radiation, or a cloud, or a plurality of factors may be reduced, or keep only a part of the meteorological factors, such as the wind direction and the wind speed. When grouping the meteorological conditions, the number of the groups may be changed as needed, such as changing a temperature grouping from 2 groups to 3 groups and more. A data resolution in the present disclosure may be 1 hour resolution or other resolutions.

Figure 2:
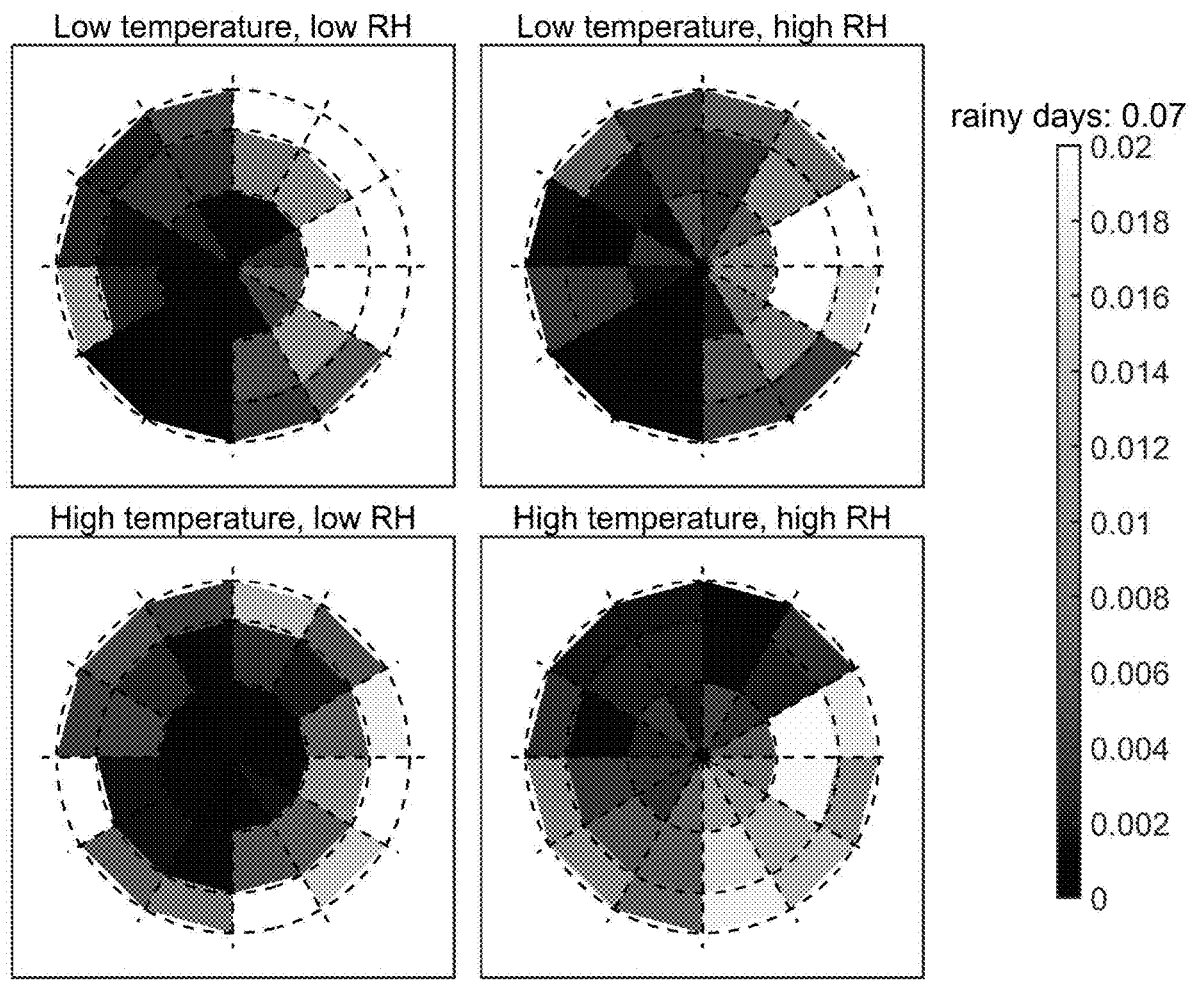
FIG. 2 illustrates a meteorology rose diagram on a frequency of occurrence of the meteorological conditions in an embodiment of the evaluation method for impact of emission control on air quality as provided in the present disclosure.

Further, in the step S100, according to a statistics to the frequency of occurrence of the meteorological conditions, a meteorology rose diagram can be drawn, as shown in FIG. 2, which shows the frequency of occurrence of the meteorological conditions. In the present embodiment, the meteorological conditions are classified into four cases, including "low temperature and low humidity; low temperature and high humidity; high temperature and low humidity; high temperature and high humidity", wherein a depth degree in the figure represents the frequency of occurrence of a meteorological condition.

In an embodiment of the present disclosure, in the step S200, acquiring information of the pollutant concentration from an environmental monitoring station, before matching the pollutant concentration with the wind speed, the wind direction, the temperature, the humidity, and the precipitation data. A specific process is as follows:

using the pollutant concentration data collected from a single environmental monitoring station, and calculating an average value of the pollutant concentration in each group of the meteorological conditions, a calculation formula is:

$$c(i) = \frac{\sum_{k=1}^{N_i} x_k}{N_i}$$

wherein c(i) is the average value of the pollutant concentration when the meteorological conditions in the group i occur, $x_k$ denotes the pollutant concentration of the group at each time point.

There are a plurality of methods to acquire the pollutant concentration data, which may be obtained from the public monitoring data of the State Environmental Protection Agency, or from the monitoring data of a plurality of provincial or municipal control points.

Further, composing all average values c(i) of the pollutant concentration in all groups, together into a pollution concentration distribution vector C, before storing the pollution concentration distribution vector C as pollution concentration distribution information.

Further, calculating a difference between the average values of the pollutant concentration in two time periods, before obtaining variation information Δc of the pollution concentration. Specifically, when the preset time period is one year, Δc is a difference of the average value of the pollutant concentration in two years, which is annual variation information of the pollution concentration. The two time periods may be two adjacent time periods, such as a first year and a second year; may also be two non-adjacent time periods, such as the first year and a third year.

Figure 3:
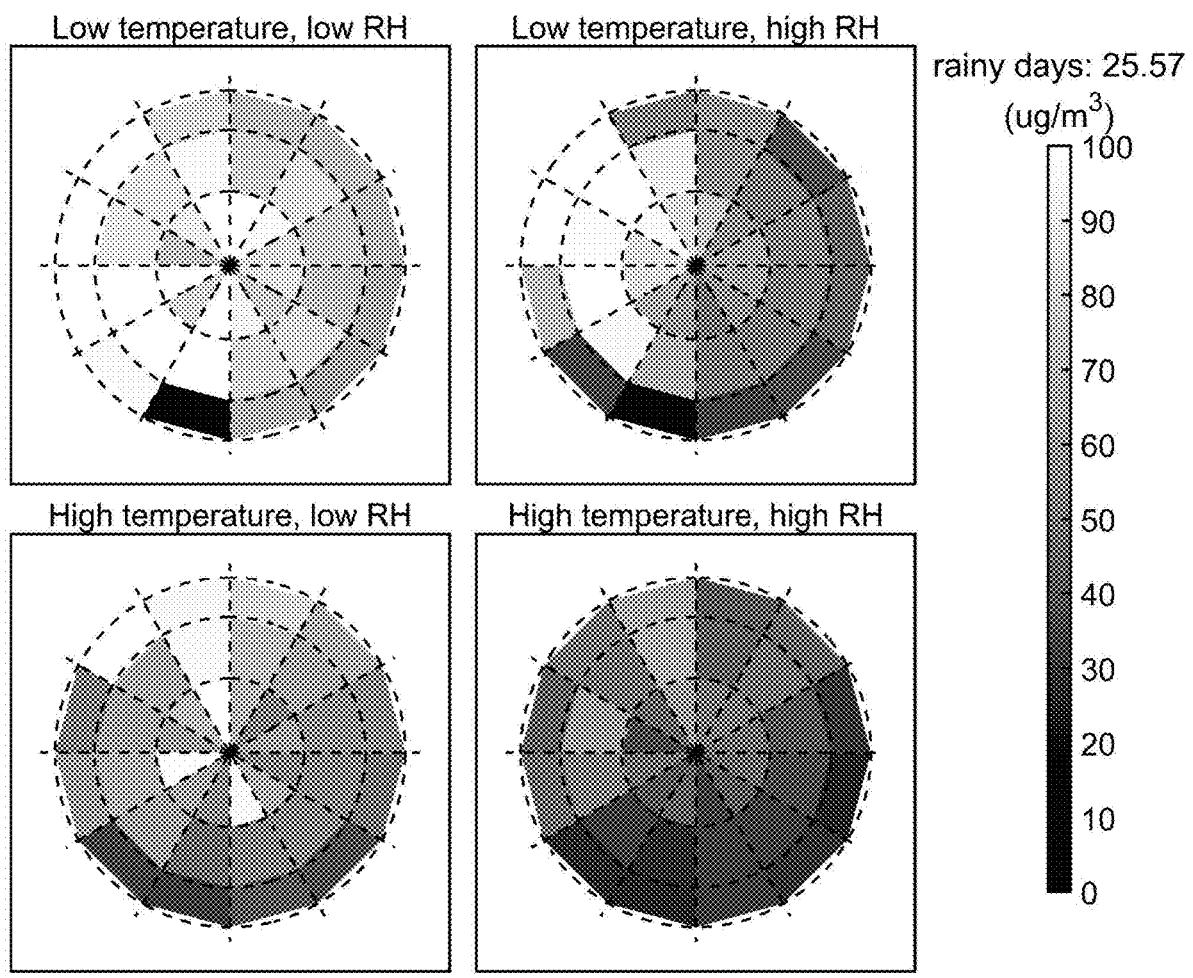
FIG. 3 illustrates a meteorology-pollution rose diagram on a concentration distribution of the pollutant in an embodiment of the evaluation method for impact of emission control on air quality as provided in the present disclosure.

In an embodiment of the present disclosure, in the step S200, according to a statistics of the pollutants concentration distribution, a meteorology-pollution rose diagram can be drawn, as shown in FIG. 3, which shows a distribution of the pollutant concentrations. In the present embodiment, the meteorological conditions are divided into four cases: "low temperature and low humidity; low temperature and high humidity; high temperature and low humidity; high temperature and high humidity", wherein a depth degree in the figure represents the pollutant concentration distribution.

In an embodiment of the present disclosure, in the step S300, performing a linear decomposition of the effect of the meteorological factors and the effect of the non-meteorological factors, according to the meteorological condition frequency distribution information, the pollution concentration distribution information and the pollution concentration variation information, by a Taylor expansion, obtaining a contribution proportion of the meteorological factors to a pollution variation and a contribution proportion of the non-meteorological factors to the pollution variation, a calculation formula is:

$$R_m = \frac{(F_2 - F_1) \cdot C_1}{\Delta c}$$

$$R_p = \frac{(C_2 - C_1) \cdot F_1}{\Delta c}$$

wherein, $R_m$ denotes the contribution proportion of the meteorological factors to the pollution variation; $R_p$ denotes the contribution proportion of the non-meteorological factors to the pollution variation; $F_1$ and $F_2$ denote two meteorological condition frequency distribution vectors in two time periods; $C_1$ and $C_2$ denote two pollution concentration distribution vectors in two time periods.

Calculating a contribution vector of the meteorological factors to the pollution variation and a contribution vector of the non-meteorological factors to the pollution variation, a calculation formula is:

$$R_m = (F_2 - F_1) * C_1$$

$$R_p = (C_2 - C_1) * F_1$$

wherein $R_m$ denotes the contribution vector of the meteorological factors to the pollution variation; $R_p$ denotes the contribution vector of the non-meteorological factors to the pollution variation.

In other words, multiplying a plurality of elements in two vectors of $F_2-F_1$ and $C_1$ respectively, before obtaining the vector $R_m$, which denotes the contribution vector of the meteorological factors to the pollution variation. And multiplying the elements in two vectors of $C_2-C_1$ and $F_1$ respectively, before obtaining the vector $R_p$, which denotes the contribution vector of the non-meteorological factors to the pollution variation.

In an embodiment of the present disclosure, when the preset time period is one year, if it is needed to calculate the pollution variation from a first year to a second year, then, $F_1$ denotes the meteorological condition frequency distribution vector of the first year, $F_2$ denotes the meteorological condition frequency distribution vector of the second year; $C_1$ denotes the pollution concentration distribution vector of the first year, $C_2$ denotes the pollution concentration distribution vector of the second year; Δc denotes an annual variation information of the pollution concentration; $R_m$ denotes the contribution vector of the meteorological factors to the annual pollution variation; $R_p$ denotes the contribution vector of the non-meteorological factors to the annual pollution variation.

Further, calculating a linear index L, a calculation formula is:

$$L = 1 - \frac{|(F_2 - F_1) \cdot (C_2 - C_1)|}{|(F_2 - F_1) \cdot C_1| + |(C_2 - C_1) \cdot F_1| + |(F_2 - F_1) \cdot (C_2 - C_1)|}$$

or $$L = 1 - \frac{|F_2 \cdot C_2 - F_1 \cdot C_2 - F_2 \cdot C_1 + F_1 \cdot C_1|}{|F_2 \cdot C_1 - F_1 \cdot C_1| + |F_1 \cdot C_2 - F_1 \cdot C_1| + |F_2 \cdot C_2 - F_1 \cdot C_2 - F_2 \cdot C_1 + F_1 \cdot C_1|}$$

saving the contribution proportion of the meteorological factors to the pollution variation $R_m$, the contribution proportion of the non-meteorological factors to the pollution variation $R_p$, the contribution vector of the meteorological factors to the pollution variation $R_m$, the contribution vector of the non-meteorological factors to the pollution variation $R_p$, and the linear index L as the meteorological and non-meteorological contribution information.

Further, a confidence level corresponding to the linear index is checked by a Monte Carlo method. Specifically, a plurality of random number is generated and assigned to four variables required for calculating the L, and the linear index L is then calculated. Repeat an experiment listed above many times, before calculating a cumulative probability distribution of L. And the cumulative probability corresponding to a certain L value is the confidence level of a linear decomposition. The confidence level corresponding to the linear index is saved as linear decomposition confidence level information.

Figure 4:
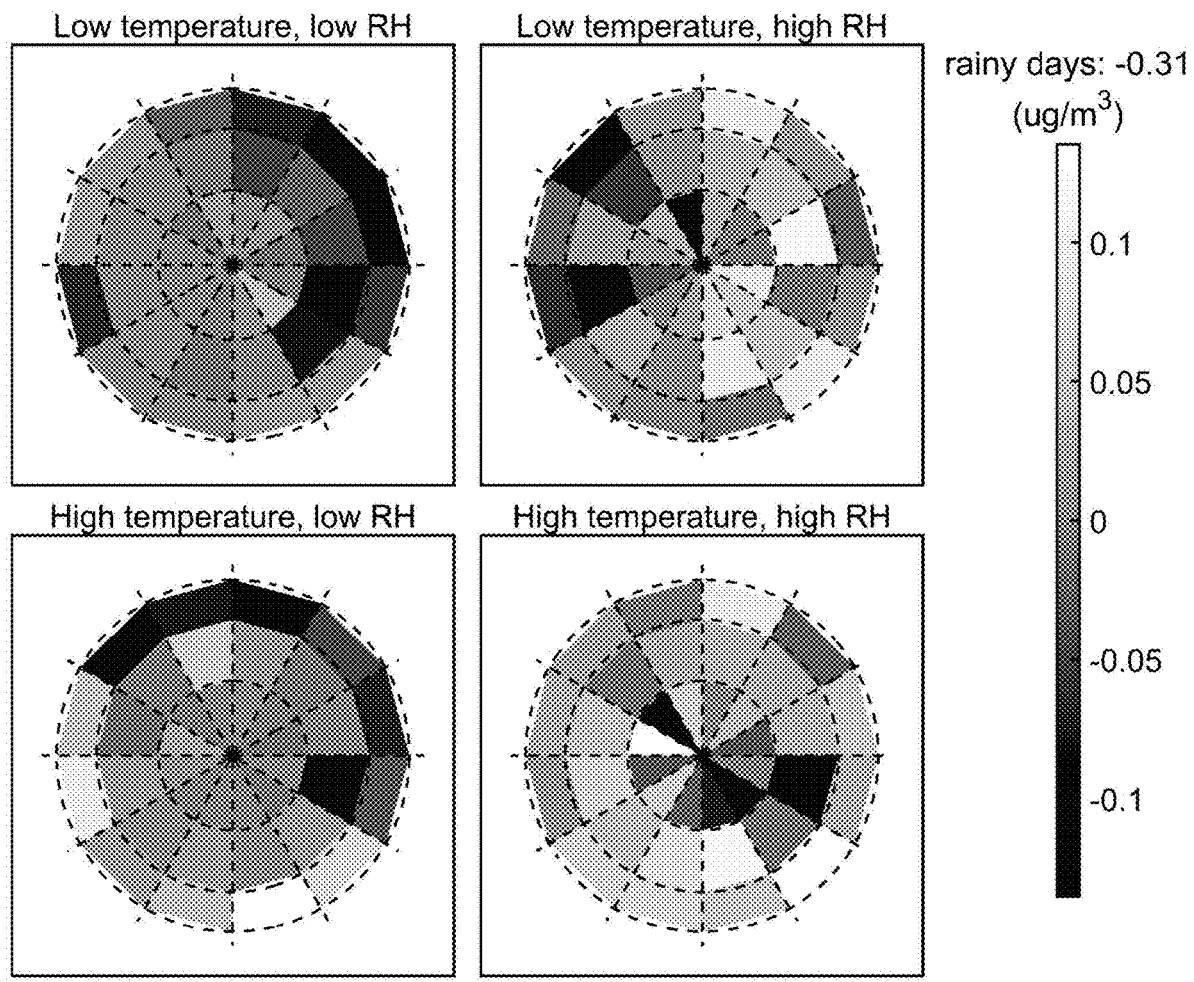
FIG. 4 illustrates a meteorology-pollution rose diagram on the contribution of meteorological factors in an embodiment of the evaluation method for impact of emission control on air quality as provided in the present disclosure.

In an embodiment of the present disclosure, in the step S300, a meteorology-pollution rose diagram may be drawn according to a decomposition of the effect of the meteorological factors and the effect of the non-meteorological factors, shown as FIG. 4, which shows a contribution of the meteorological factors. The present embodiment classifies the meteorological conditions into four cases, including "low temperature and low humidity; low temperature and high humidity; high temperature and low humidity; high temperature and high humidity", wherein a depth degree in the figure represents the pollutant concentration distribution.

In an embodiment of the present disclosure, specifically in the step S400, numbering the meteorological condition frequency distribution information, the pollution concentration distribution information, the meteorological and non-meteorological contribution information, and the linear decomposition confidence level information obtained, according to a plurality of stations and the time periods, before constructing the source emission control effect evaluation data set, for a user convenience. In an embodiment of the present disclosure, it is possible to number and list the meteorological condition frequency distribution information, the pollution concentration distribution information, the meteorological and non-meteorological contribution information, and the linear decomposition confidence level information, according to the stations and the time periods, before displaying the source emission control effect evaluation data set.

The present disclosure is a linear decomposition method based on the Taylor expansion, which decomposes the contributions of meteorological factors and non-meteorological factors to an average air quality variation; constructs a linear index L, to express an effect of a linear decomposition; tests a confidence level of the linear decomposition by the Monte Carlo method; while at a same time, considers an effect of a plurality of meteorological factors, including: the wind direction, the wind speed, the temperature, the humidity, the precipitation, and more; draws a meteorology-pollution rose diagram by using the contribution vector of the meteorological factors to the pollution variation and the contribution vector of the non-meteorological factors to the pollution variation, to display the contributions to the annual pollution variation from the meteorological factors and from the emission factors. It is able to estimate the frequency of occurrence of different weather conditions and corresponding average pollutant concentration thereof, so as to separate the contribution of the meteorological factors, represented by wind, temperature, humidity, precipitation, from the contribution of a plurality of non-meteorological anthropogenic emission control factors to the air quality variation, thereby an effect of the emission control or emission change is estimated; and the emission control effect is quantitatively evaluated by using a plurality of observation data only.

Figure 5:
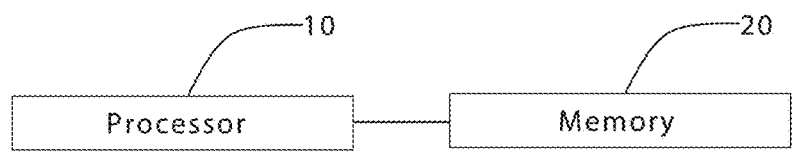
FIG. 5 illustrates a functional block diagram on an embodiment of the evaluation method for impact of emission control on air quality as provided in the present disclosure.

Shown as FIG. 5, the present disclosure further provides an evaluation device for the impact of emission control on air quality, wherein comprising a processor 10, and a memory 20 connecting to the processor 10, the memory 20 has an evaluation program for the impact of emission control on air quality stored, when the evaluation program for the impact of emission control on air quality is executed by the processor 10, a plurality of following steps are achieved:
performing a meteorological condition frequency statistics on the data collected from the meteorological station, and obtaining meteorological condition frequency distribution information;
acquiring pollutant concentration information, and performing a pollutant concentration distribution statistics based on the pollutant concentration information and the meteorological condition frequency distribution information, to obtain pollution concentration distribution information and pollution concentration variation information;
performing a decomposition of the effect of the meteorological factors and the effect of the non-meteorological factors, according to the meteorological condition frequency distribution information, the pollution concentration distribution information and the pollution concentration variation information, to obtain meteorological and non-meteorological contribution information;
constructing a source emission control effect evaluation data set, based on the meteorological condition frequency distribution information, the pollutant concentration distribution information, the meteorological and non-meteorological contribution information;
the processor 10 is applied to calling a command of the evaluation program for the impact of emission control on air quality; specifications are listed above.

Further, when the evaluation program for the impact of emission control on air quality is executed by the processor 10, a plurality of following steps are achieved:
acquiring the data collected from the meteorological station, before grouping according to a plurality of meteorological conditions, and calculating a frequency of occurrence of the meteorological conditions in each group, a calculation formula is:

$$f(i) = \frac{N_i}{\sum N_i},$$

wherein, f(i) denotes a frequency of occurrence of the meteorological conditions in a group i, $N_i$ denotes an occurrence time of the meteorological conditions in the group i during a preset time period;
composing the frequencies of occurrence of the meteorological conditions f(i) in all groups together into a meteorological condition frequency distribution vector F, and saving the meteorological condition frequency distribution vector F as the meteorological condition frequency distribution information. Details have been described above.

Further, when the evaluation program for the impact of emission control on air quality is executed by the processor 10, a plurality of following steps are achieved:
acquiring pollutant concentration information from an environmental monitoring station, calculating a pollutant concentration average value for each group of the meteorological conditions, the calculation formula is:

$$c(i) = \frac{\sum_{k=1}^{N_i} x_k}{N_i}$$

wherein c(i) is an average value of the pollutant concentration when the meteorological conditions in the group i occur, $x_k$ denotes the pollutant concentration of the group at each time point;

composing all average values c(i) of the pollutant concentration in all groups, together into a pollution concentration distribution vector C, before storing the pollution concentration distribution vector C as pollution concentration distribution information;

calculating a difference between the average values of the pollutant concentration in two time periods to obtain variation information Δc of the pollution concentration. Details have been described above.

Further, when the evaluation program for the impact of emission control on air quality is executed by the processor 10, a plurality of following steps are achieved:

performing a linear decomposition of the effect of the meteorological factors and the effect of the non-meteorological factors, according to the meteorological condition frequency distribution information, the pollution concentration distribution information and the pollution concentration variation information, by a Taylor expansion, obtaining a contribution proportion of the meteorological factors to the pollution variation and a contribution proportion of the non-meteorological factors to the pollution variation, a calculation formula is:

$$R_m = \frac{(F_2 - F_1) \cdot C_1}{\Delta c}$$

$$R_p = \frac{(C_2 - C_1) \cdot F_1}{\Delta c}$$

wherein, $R_m$ denotes the contribution proportion of the meteorological factors to the pollution variation; $R_p$ denotes the contribution proportion of the non-meteorological factors to the pollution variation; $F_1$ and $F_2$ denote two meteorological condition frequency distribution vectors in two time periods; $C_1$ and $C_2$ denote two pollution concentration distribution vectors in two time periods;

calculating a contribution vector of the meteorological factors to the pollution variation and a contribution vector of the non-meteorological factors to the pollution variation, a calculation formula is:

$$R_m = (F_2 - F_1) * C_1$$

$$R_p = (C_2 - C_1) * F_1$$

wherein $R_m$ denotes the contribution vector of the meteorological factors to the pollution variation; $R_p$ denotes the contribution vector of the non-meteorological factors to the pollution variation;

calculating a linear index L, a calculation formula is:

$$L = 1 - \frac{|(F_2 - F_1) \cdot (C_2 - C_1)|}{|(F_2 - F_1) \cdot C_1| + |(C_2 - C_1) \cdot F_1| + |(F_2 - F_1) \cdot (C_2 - C_1)|}$$

or $$L = 1 - \frac{|F_2 \cdot C_2 - F_1 \cdot C_2 - F_2 \cdot C_1 + F_1 \cdot C_1|}{|F_2 \cdot C_1 - F_1 \cdot C_1| + |F_1 \cdot C_2 - F_1 \cdot C_1| + |F_2 \cdot C_2 - F_1 \cdot C_2 - F_2 \cdot C_1 + F_1 \cdot C_1|}$$

saving the contribution proportion of the meteorological factors to the pollution variation $R_m$, the contribution proportion of the non-meteorological factors to the pollution variation $R_p$, the contribution vector of the meteorological factors to the pollution variation $R_m$, the contribution vector of the non-meteorological factors to the pollution variation $R_p$, and the linear index L as the meteorological and non-meteorological contribution information;

checking a confidence level corresponding to the linear index L by a Monte Carlo method, before saving as linear decomposition confidence level information;

numbering the meteorological condition frequency distribution information, the pollution concentration distribution information, the meteorological and non-meteorological contribution information, and the linear decomposition confidence level information obtained, according to a plurality of stations and the time periods, and constructing the source emission control effect evaluation data set. Details have been described above.

The present disclosure further provides a storage medium, wherein the storage medium has a computer program stored that may be executed to implement the evaluation method for impact of emission control on air quality as described above. Details have been described above.

All above, the present disclosure discloses an evaluation method for impact of emission control on air quality, a device and a storage medium thereof, comprising: performing a meteorological condition frequency statistics on data collected from a meteorological station, and obtaining meteorological condition frequency distribution information; acquiring pollutant concentration information, and performing a pollutant concentration distribution statistics based on the pollutant concentration information and the meteorological condition frequency distribution information, to obtain pollution concentration distribution information and pollution concentration variation information; performing a decomposition of the effect of meteorological factors and the effect of non-meteorological factors, according to the meteorological condition frequency distribution information, the pollution concentration distribution information and the pollution concentration variation information, to obtain meteorological and non-meteorological contribution information; constructing a source emission control effect evaluation data set, based on the meteorological condition frequency distribution information, the pollutant concentration distribution information, the meteorological and non-meteorological contribution information. The present disclosure is able to quantitatively evaluate the impact of the emission control based on observation data.

It should be understood that, the application of the present disclosure is not limited to the above examples listed. It will be possible for a person skilled in the art to make modification or replacements according to the above descriptions, which shall all fall within the scope of protection in the appended claims of the present disclosure.

What is claimed is:

1. An evaluation method for an impact of emission control on air quality, comprising:
    performing meteorological condition frequency statistics on data collected from a meteorological station; and obtaining meteorological condition frequency distribution information;
    acquiring pollutant concentration information; and
    performing pollutant concentration distribution statistics based on the acquired pollutant concentration information and the obtained meteorological condition frequency distribution information to calculate both pollution concentration distribution information and pollution concentration variation information;
    performing a decomposition of an effect of a plurality of meteorological factors and an effect of a plurality of non-meteorological factors, according to the obtained meteorological condition frequency distribution information, the calculated pollution concentration distribution information, and the calculated pollution concentration variation information, to obtain both meteorological contribution information and non-meteorological contribution information; and constructing a source emission control effect evaluation data set based on the meteorological condition frequency distribution information, the pollutant concentration distribution information, the meteorological contribution information, and the non-meteorological contribution information; and displaying a pollutant rose diagram based on the source emission control effect evaluation data, wherein the displayed pollutant rose diagram depicts an estimated effect of the emission control and contributions to annual pollution variation from the meteorological factors and emission factors.

2. The evaluation method according to claim 1, wherein performing the meteorological condition frequency statistics on the data collected from the meteorological station, and obtaining the meteorological condition frequency distribution information, further comprises:

acquiring the data collected from the meteorological station before grouping according to a plurality of meteorological conditions;

calculating a frequency of occurrence of the meteorological conditions f(i) in each group;

composing the frequencies of occurrence of the meteorological conditions f(i) in all groups together into a meteorological condition frequency distribution vector F; and saving the meteorological condition frequency distribution vector F as the meteorological condition frequency distribution information.

3. The evaluation method according to claim 2, wherein acquiring the pollutant concentration information, performing the pollutant concentration distribution statistics based on the pollutant concentration information and the meteorological condition frequency distribution information, to obtain the pollution concentration distribution information and the pollution concentration variation information, further comprises:

acquiring pollutant concentration information from an environmental monitoring station;

calculating a pollutant concentration average value c(i) for each group of the meteorological conditions;

composing all average values c(i) of the pollutant concentration in all groups, together into a pollution concentration distribution vector C, before storing the pollution concentration distribution vector C as pollution concentration distribution information; and calculating a difference between the average values of the pollutant concentration in two time periods to obtain variation information Ac of the pollution concentration.

4. The evaluation method according to claim 3, wherein performing the decomposition of the effect of the meteorological factors and the effect of the non-meteorological factors, according to the meteorological condition frequency distribution information, the pollution concentration distribution information and the pollution concentration variation information, to obtain the meteorological and non-meteorological contribution information, further comprises:

performing a linear decomposition of the effect of the meteorological factors and the effect of the non-meteorological factors, according to the meteorological condition frequency distribution information, the pollution concentration distribution information and the pollution concentration variation information, by a Taylor expansion;

obtaining a contribution proportion of the meteorological factors to a pollution variation $R_m$ and a contribution proportion of the non-meteorological factors to the pollution variation $R_p$;

calculating a contribution vector of the meteorological factors to the pollution variation $R_m$ and a contribution vector of the non-meteorological factors to the pollution variation $R_p$;

calculating a linear index L, saving the contribution proportion of the meteorological factors to the pollution variation $R_m$, the contribution proportion of the non-meteorological factors to the pollution variation $R_p$, the contribution vector of the meteorological factors to the pollution variation $R_m$, the contribution vector of the non-meteorological factors to the pollution variation $R_p$, and the linear index L as the meteorological and non-meteorological contribution information; and checking a confidence level corresponding to the linear index L by a Monte Carlo method, before saving as linear decomposition confidence level information.

5. The evaluation method according to claim 4, wherein constructing the source emission control effect evaluation data set, based on the meteorological condition frequency distribution information, the pollutant concentration distribution information, the meteorological and non-meteorological contribution information, further comprises:

numbering the meteorological condition frequency distribution information, the pollution concentration distribution information, the meteorological and non-meteorological contribution information, and the linear decomposition confidence level information obtained according to a plurality of stations and the time periods, before constructing the source emission control effect evaluation data set.

6. An evaluation device for the impact of emission control on air quality, comprising a processor, and a memory connecting to the processor, the memory has an evaluation program for the impact of emission control on air quality stored, when the evaluation program for the impact of emission control on air quality is executed by the processor, configured to perform:

performing meteorological condition frequency statistics on data collected from a meteorological station; and obtaining meteorological condition frequency distribution information;

acquiring pollutant concentration information; and performing pollutant concentration distribution statistics based on the pollutant concentration information and the meteorological condition frequency distribution information, to obtain pollution concentration distribution information and pollution concentration variation information;

performing a decomposition of the effect of the meteorological factors and the effect of the non-meteorological factors, according to the meteorological condition frequency distribution information, the pollution concentration distribution information and the pollution concentration variation information, to obtain meteorological and non-meteorological contribution information;

constructing a source emission control effect evaluation data set, based on the meteorological condition frequency distribution information, the pollutant concentration distribution information, the meteorological and non-meteorological contribution information; and the processor is applied to calling a command of the evaluation program for the impact of emission control on air quality; and displaying a pollutant rose diagram based on the source emission control effect evaluation data, wherein the displayed pollutant rose diagram depicts an estimated effect of the emission control and contributions to annual pollution variation from the meteorological factors and emission factors.

7. The evaluation device according to claim 6, when the evaluation program for the impact of emission control on air quality is executed by the processor, configured to perform:

acquiring the data collected from the meteorological station, before grouping according to a plurality of meteorological conditions, and calculating a frequency of occurrence of the meteorological conditions f(i) in each group; and composing the frequencies of occurrence of the meteorological conditions f(i) in all groups together into a meteorological condition frequency distribution vector F; and saving the meteorological condition frequency distribution vector F as the meteorological condition frequency distribution information.

8. The evaluation device according to claim 7, wherein when the evaluation program for the impact of emission control on air quality is executed by the processor, configured to perform:

acquiring pollutant concentration information from an environmental monitoring station, calculating a pollutant concentration average value c(i) for each group of the meteorological conditions;

composing all average values c(i) of the pollutant concentration in all groups, together into a pollution concentration distribution vector C, before storing the pollution concentration distribution vector C as pollution concentration distribution information; and calculating a difference between the average values of the pollutant concentration in two time periods to obtain variation information Δc of the pollution concentration.

9. The evaluation device according to claim 8, wherein when the evaluation program for the impact of emission control on air quality is executed by the processor, configured to perform:

performing a linear decomposition of the effect of the meteorological factors and the effect of the non-meteorological factors, according to the meteorological condition frequency distribution information, the pollution concentration distribution information and the pollution concentration variation information, by a Taylor expansion, obtaining a contribution proportion of the meteorological factors to the pollution variation $R_m$ and a contribution proportion of the non-meteorological factors to the pollution variation;

calculating a contribution vector of the meteorological factors to the pollution variation $R_m$ and a contribution vector of the non-meteorological factors to the pollution variation $R_p$;

calculating a linear index L, saving the contribution proportion of the meteorological factors to the pollution variation $R_m$, the contribution proportion of the non-meteorological factors to the pollution variation $R_p$, the contribution vector of the meteorological factors to the pollution variation $R_m$, the contribution vector of the non-meteorological factors to the pollution variation $R_p$, and the linear index L as the meteorological and non-meteorological contribution information;

checking a confidence level corresponding to the linear index L by a Monte Carlo method, before saving as linear decomposition confidence level information; and numbering the meteorological condition frequency distribution information, the pollution concentration distribution information, the meteorological and non-meteorological contribution information, and the linear decomposition confidence level information obtained, according to a plurality of the stations and the time periods, and constructing the source emission control effect evaluation data set.

10. A non-transitory storage medium having a computer program stored therein that may be executed by a processor to implement an evaluation method for impact of emission control on air quality comprising:

performing meteorological condition frequency statistics on data collected from a meteorological station, and obtaining meteorological condition frequency distribution information;

acquiring pollutant concentration information, and performing pollutant concentration distribution statistics based on the pollutant concentration information and the meteorological condition frequency distribution information, to obtain pollution concentration distribution information and pollution concentration variation information;

performing a decomposition of an effect of a plurality of meteorological factors and an effect of a plurality of non-meteorological factors, according to the meteorological condition frequency distribution information, the pollution concentration distribution information and the pollution concentration variation information, to obtain meteorological and non-meteorological contribution information;

constructing a source emission control effect evaluation data set based on the meteorological condition frequency distribution information, the pollutant concentration distribution information, the meteorological and non-meteorological contribution information; and displaying a pollutant rose diagram based on the source emission control effect evaluation data, wherein the displayed pollutant rose diagram depicts an estimated effect of the emission control and contributions to annual pollution variation from the meteorological factors and emission factors.

* * * * *